United States Patent
Jeanne et al.

(10) Patent No.: US 11,140,973 B2
(45) Date of Patent: Oct. 12, 2021

(54) MEASURING HEALTH PARAMETER USING TISSUE RECOVERY TIME

(71) Applicant: KONINKLIJKE PHILIPS N.V., Eindhoven (NL)

(72) Inventors: Vincent Jeanne, Migne Auxances (FR); Yekaterina Aleksandrovna Borisenko, Lynnwood, WA (US); Steven Charles Deane, Cambridge (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 10 days.

(21) Appl. No.: 16/318,011

(22) PCT Filed: Mar. 13, 2018

(86) PCT No.: PCT/EP2018/056134
§ 371 (c)(1),
(2) Date: Jan. 15, 2019

(87) PCT Pub. No.: WO2018/172127
PCT Pub. Date: Sep. 27, 2018

(65) Prior Publication Data
US 2020/0000215 A1  Jan. 2, 2020

Related U.S. Application Data

(60) Provisional application No. 62/473,650, filed on Mar. 20, 2017.

(30) Foreign Application Priority Data

May 5, 2017 (EP) ..................................... 17169745

(51) Int. Cl.
*A46B 15/00* (2006.01)
*A61B 5/00* (2006.01)

(52) U.S. Cl.
CPC ........ *A46B 15/0004* (2013.01); *A61B 5/0053* (2013.01); *A61B 5/0088* (2013.01);
(Continued)

(58) Field of Classification Search
CPC .. A46B 15/0004; A61B 5/0053; A61B 5/0088
See application file for complete search history.

(56) References Cited

U.S. PATENT DOCUMENTS 6,631,288 B1    10/2003  Bain et al.
7,302,287 B2 *  11/2007  Gandjbakhche ..... A61B 5/0088
                                                600/407

(Continued)

FOREIGN PATENT DOCUMENTS

CN   104546198 A   4/2015
CN   105662630 A   6/2016
(Continued)

*Primary Examiner* — Daniel L Cerioni
*Assistant Examiner* — Yasmeen S Warsi (57) ABSTRACT

An oral care device (10) assesses a health parameter of gingival tissue of a user by means of a force-generating module (52) to apply a momentary force to the gingival tissue by applying a burst of compressed air or a burst of liquid to the gingival tissue, a sensor (28) to obtain a plurality of optical signals from the gingival tissue over time after the momentary force has been applied, a controller (30) to quantify, based at least in part on an analysis of the plurality of optical signals, the health parameter (e.g. inflammation of the gingival tissue), wherein the health parameter is based at least in part on an amount of time the gingival tissue takes to recover to the application of force; and a feedback module (46) to provide information to the user regarding the quantified health parameter.

15 Claims, 6 Drawing Sheets

(52) U.S. Cl.
CPC ............ *A61B 5/6898* (2013.01); *A61B 5/441* (2013.01); *A61B 5/682* (2013.01); *A61B 5/6885* (2013.01); *A61B 2560/029* (2013.01)

(56) References Cited

U.S. PATENT DOCUMENTS

| | | | |
|---|---|---|---|
| 7,483,733 | B2 | 1/2009 | Shani et al. |
| 2006/0234383 | A1 | 10/2006 | Gough |
| 2010/0190129 | A1 | 7/2010 | Paz |
| 2011/0311939 | A1* | 12/2011 | Hunter ................ A61C 19/063 433/27 |
| 2015/0044629 | A1 | 2/2015 | Wang |
| 2015/0297085 | A1 | 10/2015 | Simons et al. |
| 2016/0038033 | A1 | 2/2016 | Lal |
| 2016/0100790 | A1 | 4/2016 | Cantu et al. |

FOREIGN PATENT DOCUMENTS

| | | |
|---|---|---|
| EP | 0049905 A1 | 4/1982 |
| WO | 2016087556 A1 | 6/2016 |

* cited by examiner

MEASURING HEALTH PARAMETER USING TISSUE RECOVERY TIME

CROSS-REFERENCE TO PRIOR APPLICATIONS

This application is the U.S. National Phase application under 35 U.S.C. § 371 of International Application No. PCT/EP2018/056134, filed on Mar. 13, 2018, which claims the benefit of European Patent Application No. 17169745.1, filed on May 5, 2017 and U.S. Provisional Application No. 62/473,650, filed on Mar. 20, 2017. These applications are hereby incorporated by reference herein.

FIELD OF THE INVENTION

The present disclosure is directed generally to oral care methods and systems for assessing a health parameter of gingival tissue.

BACKGROUND

US 2006/0234383 discloses a skin tissue assessment device consists of a fluid pressure system, an optical system, and a micro-controller. Compression of bladder by actuator displaces the fluid within the bladder into chamber causing diaphragm to inflate and apply pressure onto the tissue surface in order to initiate a blanch. The diaphragm is deflated after a predetermined time, either by releasing the actuator or opening exhaust valve. Throughout the blanching, the optical system illuminates the blanch area and the returned light data is collected at regular intervals for several wavelengths from the point when the blanch is initiated, throughout the blanching and a predetermined time thereafter during the recovery phase. The micro-controller controls the process and analyses the returned signals to provide assessment of the tissue surface area.

It is estimated that 50% of the adult population in the United States is affected by periodontal disease, with severity of disease ranging from gingivitis to periodontitis. However, consumers are often not able to detect early signs of periodontal disease. Accordingly, such diseases may only be detected during dental visits when the disease is already advanced and significantly harder to treat.

Inflammation of tissues within the mouth is one of the key signs of periodontal disease. Detecting inflammation could signal the possible existence of a disease state, and would alert the individual to the need for consulting a professional for attribution of the deviation to a particular clinical picture and any necessary treatment, as finding inflammation is merely a finding of a deviation from a normal situation, and does not yet provide any indication as to the cause of the inflammation and thus does not yet enable to determine the appropriate treatment. However, existing oral care devices are unable to identify or quantify inflammation of tissues, and thus periodontal disease is not detected.

SUMMARY OF THE INVENTION

Accordingly, there is a continued need in the art for improved oral care methods and devices that assess a health parameter of gingival tissue. The invention is defined by the independent claims. The dependent claims define advantageous embodiments.

The present disclosure is directed to inventive methods and systems for assessing a health parameter such as inflammation using capillary refill time. Various embodiments and implementations herein are directed to an oral care device configured to assess the health of gingival tissue during an oral care routine. The oral care device comprises a force-generating module that applies a direct or remote force to gingival tissue by applying a burst of compressed air or a burst of liquid to the gingival tissue. The oral care device also comprises a sensor that quantifies capillary refill time of the gingival tissue following the application of force. The oral care device analyzes the capillary refill time and determines whether there is inflammation or any other detectable health parameter to report. The oral care device may alert the user in real-time or via a post-cleaning report to the existence of inflammation. The oral care device may also comprise a sensor that quantifies a baseline or status of the gingival tissue prior to the application of force.

The invention may further include obtaining, with the sensor, a baseline optical signal from the tissue prior to the application of force.

The invention may further include detecting a proximity to the tissue.

The invention may further include communicating the quantified health parameter to a remote third party.

The sensor may comprise a light source and an optical sensor.

The force-generating module may apply force via the expulsion of air.

Quantifying a health parameter of the user may comprise a determination of an amount of time the tissue takes to reach a predetermined perfusion threshold following the application of force, or an amount of time the tissue takes to reach a stable perfusion level following the application of force. Quantifying a health parameter of the user may comprise a determination of an amount of time the tissue takes to substantially match the obtained baseline optical signal.

The health parameter may be inflammation of gingival tissue.

The term "controller" is used generally to describe various apparatus relating to the operation of an oral care apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

The term "user interface" refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a system for assessing inflammation of gingival tissues using an oral care device. More generally, Applicant has recognized and appreciated that it would be beneficial to provide a system to assess one or more health parameters using capillary refill time. Accordingly, one aspect of the invention described or otherwise envisioned herein provide a device such as an oral care device configured to measure capillary refill time of a tissue, such as gingival tissue. The oral care device may comprise a force-generating module that applies a direct or remote force to gingival tissue, and a sensor that quantifies capillary refill time of the gingival tissue following the application of force. Based on the capillary refill time, the oral care device can determine whether there is inflammation or any other detectable health parameter to report, and can share that information with the user or a third party. The oral care device may also include a sensor that quantifies a baseline or status of the tissue prior to the application of force.

The embodiments and implementations disclosed or otherwise envisioned herein can be utilized with any oral device, including but not limited to a toothbrush, a flossing device such as a Philips AirFloss®, an oral irrigator, or any other oral device. One particular goal of utilization of the embodiments and implementations herein is to assess inflammation of gingival tissues using an oral care device such as, e.g., a Philips Sonicare® toothbrush. However, the disclosure is not limited to a toothbrush and thus the disclosure and embodiments disclosed herein can encompass any oral device.

Figure 1:
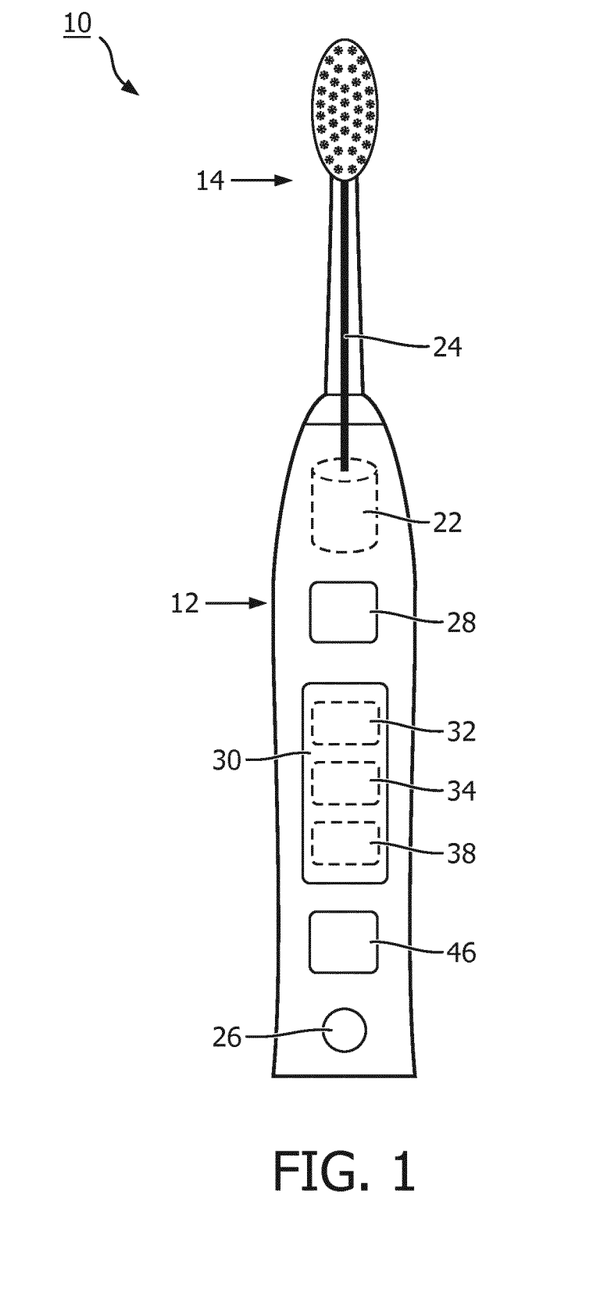
FIG. 1 is a schematic representation of an oral care device, in accordance with an embodiment.

FIG. 1 shows an embodiment of an oral care device 10 with a body portion 12 and a head member 14 mounted on the body portion. Head member 14 typically includes at its end remote from the body portion an element for oral care (e.g. a brush head).

Head member 14 may be mounted so as to be able to move relative to the body portion 12. The movement can be any of a variety of different movements, including vibrations or rotation, among others. Head member 14 may be mounted or the body so as to be able to vibrate relative to body portion 12. The head member 14 can be fixedly mounted onto body portion 12, or it may alternatively be detachably mounted so that head member 14 can be replaced with a new one when the cleaning components of the device are worn out and require replacement.

Body portion 12 may include a drivetrain 22 for generating movement and a transmission component 24 for transmitting the generated movements to head member 14. For example, drivetrain 22 can comprise a motor or electromagnet(s) that generates movement of the transmission component 24, which is subsequently transmitted to the brush head member 14. Drivetrain 22 can include components such as a power supply, an oscillator, and one or more electromagnets, among other components. In this embodiment the power supply comprises one or more rechargeable batteries, not shown, which can, for example, be electrically charged in a charging holder in which oral care device 10 is placed when not in use.

Although in the present embodiment the oral care device 10 is an electric toothbrush, it will be understood that in an alternative embodiment the oral care device is a manual toothbrush (not shown). In such an arrangement, the manual toothbrush has electrical components, but the brush head is not mechanically actuated by an electrical component.

Body portion 12 is further provided with a user input 26 to activate and de-activate movement generator 22. The user input 26 allows a user to operate the oral care device 10, for example to turn the oral care device 10 on and off. The user input 26 may, for example, be a button, touch screen, or switch.

The oral care device 10 includes one or more sensors 28. Sensor 28 is shown in FIG. 1 within body portion 12, but may be located anywhere within the device, including for example within head member 14. Many different types of sensors could be utilized, as described or otherwise envisioned herein. These sensors may provide complementary information about the position of the device with respect to a user's body part, a fixed point, and/or one or more other positions. Sensor 28 may be disposed in a predefined position and orientation in the oral care device 10, and the brush head is in a fixed spatial relative arrangement to sensor 28. Therefore, the orientation and position of the brush head can be easily determined based on the known orientation and position of the sensor 28.

The information generated by the first sensor 28 is provided to a controller 30. Controller 30 may be formed of one or multiple modules, and is configured to operate the oral care device 10 in response to an input, such as input obtained via user input 26. The sensor 28 may be integral to the controller 30. Controller 30 can comprise, for example, at least a processor 32, a memory 34, and a connectivity module 38. The processor 32 may take any suitable form, including but not limited to a microcontroller, multiple microcontrollers, circuitry, a single processor, or plural processors. The memory 34 can take any suitable form, including a non-volatile memory and/or RAM. The non-volatile memory may include read only memory (ROM), a hard disk drive (HDD), or a solid state drive (SSD). The memory can store, among other things, an operating system.

The RAM is used by the processor for the temporary storage of data. An operating system may contain code which, when executed by controller 30, controls operation of the hardware components of oral care device 10. Connectivity module 38 may transmit collected sensor data, and can be any module, device, or means capable of transmitting a wired or wireless signal, including but not limited to a Wi-Fi, Bluetooth, near field communication, and/or cellular module.

Oral care device 10 may include a user interface 46 configured to provide information to a user before, during, and/or after a cleaning session. The user interface 46 can take many different forms, but is configured to provide information to a user. For example, the information can be read, viewed, heard, felt, and/or otherwise interpreted concerning inflammation of one or more tissues within the mouth. The user interface 46 may provide feedback to the user that includes information about where tissues are inflamed, and/or how much inflammation is present. Accordingly, the user interface may be a display that provides information to the user, a haptic mechanism that provides haptic feedback to the user, a speaker to provide sounds or words to the user, or any of a variety of other user interface mechanisms. The user interface 46 may include sending information from the oral care device to a user's smartphone by means of a wireless method (e.g. Bluetooth, WiFi), whereby the smartphone rather than the oral care device provides the information to the user. In a system comprising an oral care device and a smartphone, all or part of the tasks of the controller 30 may be carried out by the smartphone.

Figure 2:
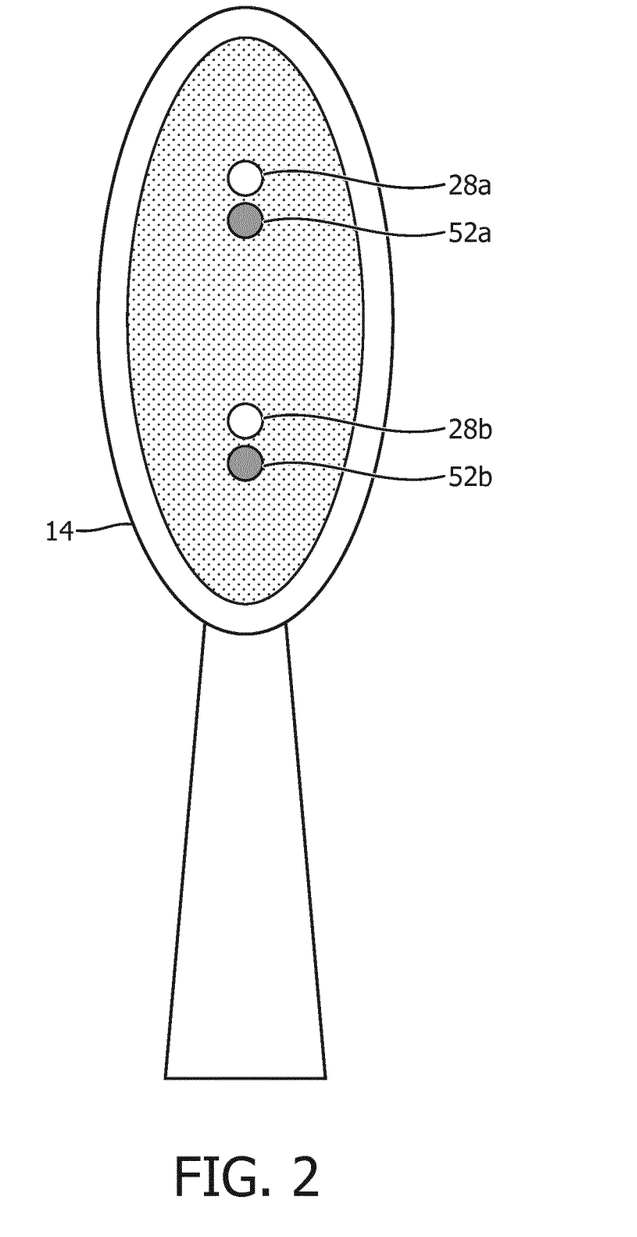
FIG. 2 is a schematic representation of a brush head of an oral care device, in accordance with an embodiment.

FIG. 2 shows an embodiment of a head member 14 of an oral care device. Head member 14 comprises one or more sensors 28, and one or more force-generation modules 52. Although head member 14 in FIG. 2 comprises two sensors 28a and 28b, and two force-generation modules 52a and 52b, the device may comprise a single sensor and module, or a plurality of sensors and modules. Additionally, although the sensor and module are shown within the head member 14 of the oral care device, it should be noted that the sensor and module could be located elsewhere on the device. Additionally, although the sensor and force-generation module are shown in very close proximity, in some embodiments the sensor and force-generation module could be located remotely from one another.

The sensor 28 is any sensor capable of quantifying capillary refill time of tissue following an application of force. Sensor 28 may also be configured to obtain a baseline of the issue prior to the application of force. Sensor 28 may be a single sensor or a sensor array. Sensor 28 may comprise one or more light sources 54 (shown in FIG. 3). The light source is configured to illuminate the tissue at a wavelength that allows for detection of capillary refill. Sensor 28 may also comprise one or more optical sensors 56 (shown in FIG. 3) configured to detect capillary refill.

For example, sensor 28 can characterize capillary refill of gingival tissue using a color ratio over either a specific band of wavelengths (such as red over green), or a dedicated set of wavelengths (such as 480 nm over 660 nm).

To obtain a baseline tissue measurement, sensor 28 obtains information about the color or other appearance of the gingival tissue prior to the application of force. Sensor 28 may obtain an image or average R, G, and B values if the optical sensor targets the visible spectrum. Sensor 28 may also or alternatively measure reflectivity values at a given wavelength if there is a multi-spectral sensor. For example, the multi-spectral sensor could be a spectrometer or photocell in combination with a set of given LEDs providing illumination at given wavelengths. The force-generation module may utilize liquid as a medium to apply force. Sensor 28 may thus utilize polarized light and include a cross-polarizer located in front of the optical sensor to reduce the impact of specular reflections.

The force-generation module 52 applies a brief force to the tissue. Force-generation module 52 applies a burst of compressed air or a burst of liquid to the tissue. Using liquid to apply force may result in specular reflections which could reduce the signal to noise ratio of the measurement, and thus compressed air might be preferred in some embodiments. In a practical embodiment, the system is incorporated in an interdental cleaning device like the Philips Airfloss, which uses (bursts of) air and micro-droplets of fluid, and measurement takes place before cleaning each interdental space. By doing so, measurements can be made without a user noticing anything as they take place during a normal flossing routine as the measurements would use the same flow of air and micro-droplets of fluid as already used for flossing.

Figure 3:
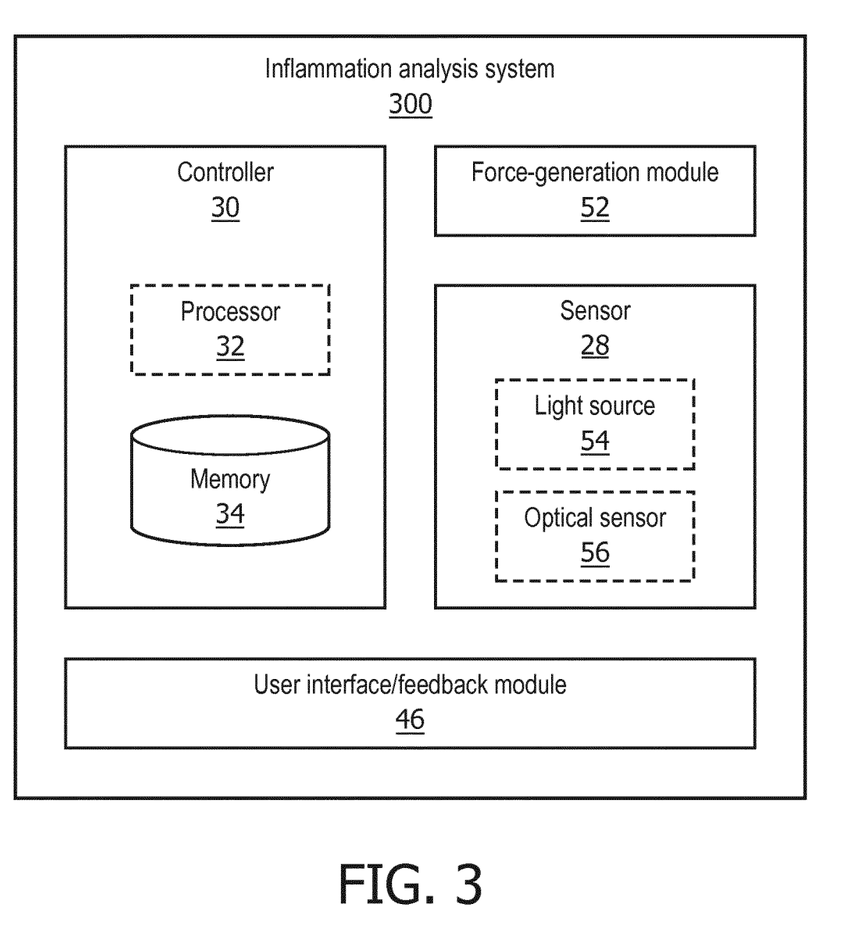
FIG. 3 is a schematic representation of an inflammation analysis system, in accordance with an embodiment.

FIG. 3 shows an embodiment of an inflammation analysis system 300. Inflammation analysis system 300 may include a controller 30 comprising a processor 32 and a memory 34. The inflammation analysis system 300 also comprises a force-generation module 52 configured to apply a force on one or more tissues. The inflammation analysis system 300 also comprises a sensor 28 configured to obtain information about the tissue before and/or after the application of force, and can include a light source 54 and an optical sensor 56, which may be an optical sensor, a multi-spectral sensor, or any other sensor. The inflammation analysis system 300 also includes a user interface 46, which provides information to the user about the status of the tissue. User interface 46 can be or can comprise a feedback module that provides direct feedback to the user via a haptic signal, audio signal, visual signal, and/or any other type of signal.

Inflammation analysis system 300 can be implemented in a mechanical or electric toothbrush 10, as shown in FIG. 1. Alternatively, inflammation analysis system 300 can be implemented as any device configured to come into proximity with tissues that can be quantified. For example, inflammation analysis system 300 can be implemented as another oral care device such as a flossing device, an oral irrigator, a tongue cleaner, or any other oral care device. Inflammation analysis system 300 can be implemented as a shaver, a skin care device, or any other device.

Figure 4:
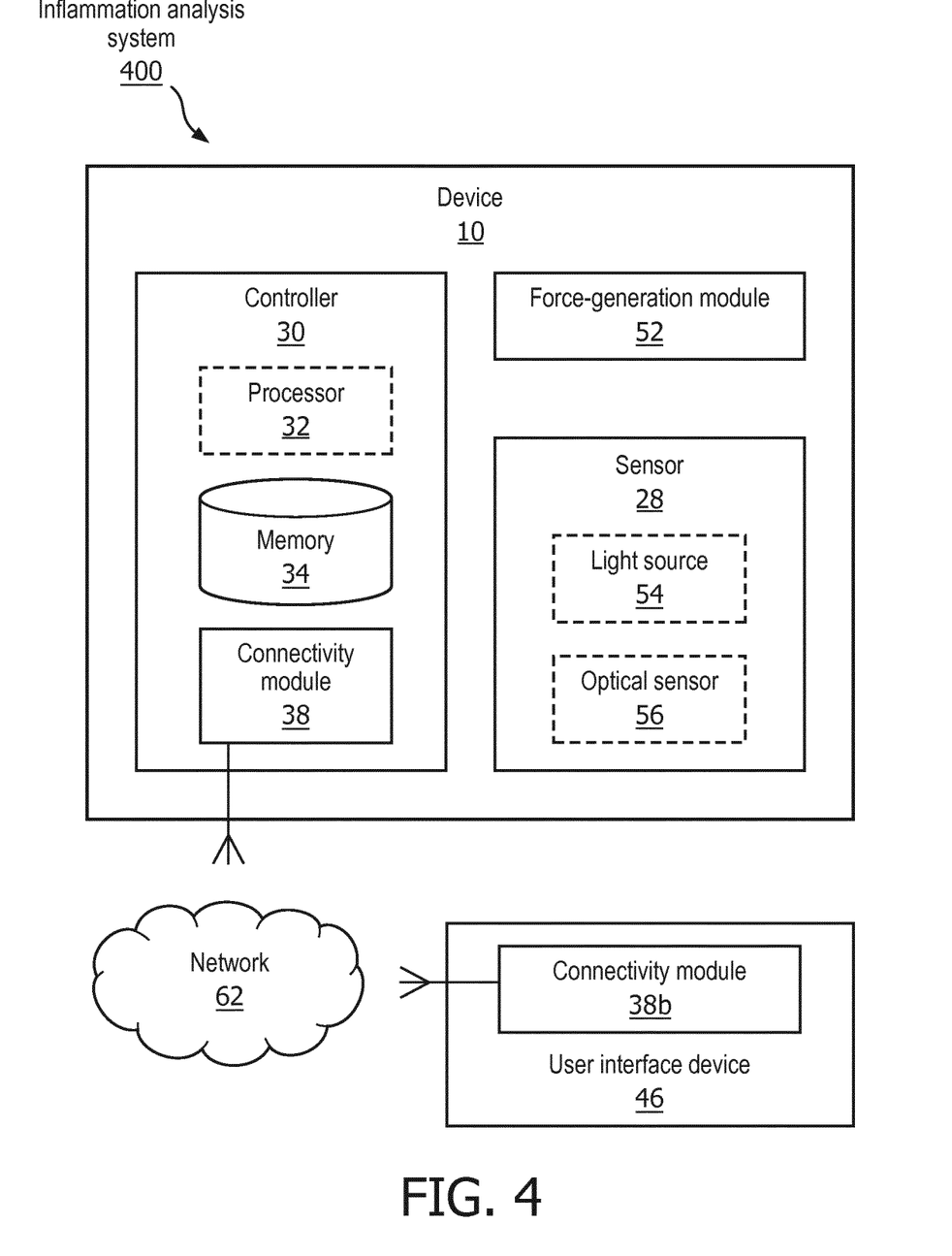
FIG. 4 is a schematic representation of an inflammation analysis system, in accordance with an embodiment.

FIG. 4 shows an embodiment of an inflammation analysis system 400. Inflammation analysis system 400 may comprise a device 10 and a user interface device 46. Device 10 includes a controller 30 comprising a processor 32, a memory 34, and a connectivity module 38. The inflammation analysis system 400 also comprises a force-generation module 52 configured to apply a force on one or more tissues. The inflammation analysis system 400 also comprises a sensor 28 configured to obtain information about the tissue before and/or after the application of force, and can include a light source 54 and an optical sensor 56, which may be an optical sensor, a multi-spectral sensor, or any other sensor.

User interface device 46 is configured to communicate information to a user of device 10. Accordingly, user interface device comprises a feedback mechanism that provides direct feedback to the user via a haptic signal, audio signal, visual signal, and/or any other type of signal. User interface device 46 may be any device, including but not limited to a base or charging station, a smartphone, a tablet, a laptop, a desktop, a wearable device, a smart mirror, or any other device.

The connectivity modules 38 and 38b can be any module, device, or means capable of transmitting a wired or wireless signal, including but not limited to a Wi-Fi, Bluetooth, near field communication, and/or cellular module. The connectivity module of device 10 is configured, programmed, or designed to communicate with the user interface device 46, and the connectivity module 38b of the user interface device 46 is configured, programmed, or designed to communicate with device 60. The connectivity modules may communicate directly via a wired and/or wireless connection, or they may communicate via a wired and/or wireless network 62. For example, user interface device 46 may be a smartphone, and connectivity module 38 of device 10 may communicate with the smartphone via Bluetooth. Connectivity module 38 of device 10 may communicate with a router via a WiFi signal, and that signal can then be transmitted to a local or remote receiver.

Figure 5:
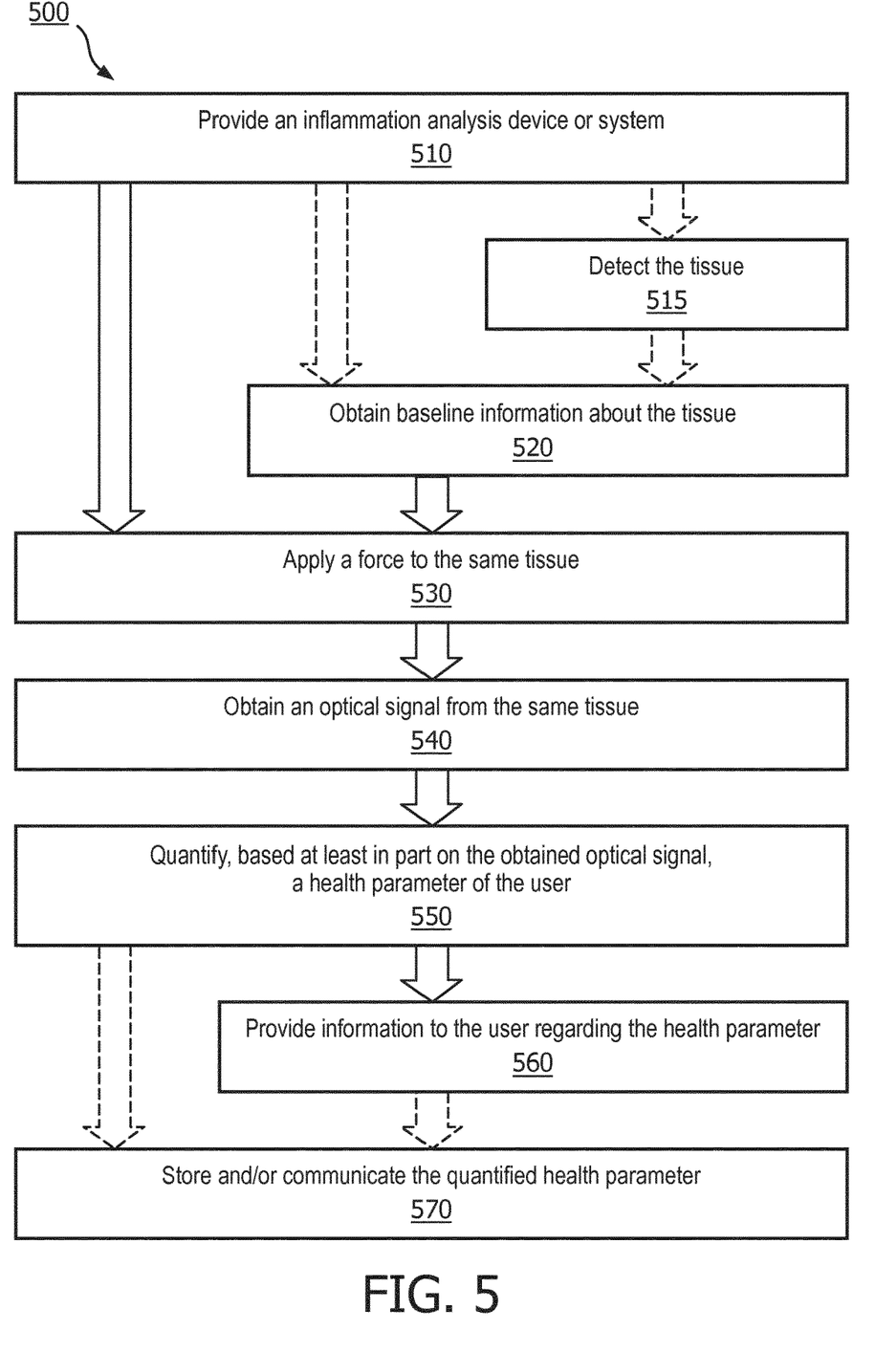
FIG. 5 is a flowchart of a method for assessing a health parameter of a user, in accordance with an embodiment.

Referring to FIG. 5, in one embodiment, is a flowchart of a method 500 for assessing a health parameter using capillary refill time. In step 510, a health parameter analysis system is provided. The health parameter analysis system may be any of the devices or systems described or otherwise envisioned herein. For example, the health parameter analysis system may be an inflammation analysis system 300 or 400, or oral care device 10. Although method 500 is described within the framework of an oral care device 10, the method can be implemented using any other health parameter analysis system.

In step 520 of the method, the system obtains a baseline optical signal or other baseline information from the tissue to be analyzed. The baseline optical signal or information is obtained by sensor 28, and comprises one or more optical signals or other spectral sensor data. For example, sensor 28 may comprise a light source 54 configured to illuminate the tissue. The sensor may obtain R, G, and B values if the optical sensor targets the visible spectrum, or may measure reflectivity values at a given wavelength if there is a multispectral sensor. The sensor may obtain a baseline using a color ratio over either a specific band of wavelengths (such as red over green), or a dedicated set of wavelengths (such as 480 nm over 660 nm). The baseline information may be stored temporarily or permanently for additional analysis. The system may continuously obtain baseline information, may periodically obtain baseline information, and/or may obtain baseline information only in response to a trigger.

For example, at optional step 515 of the method, the system detects tissue and activates sensor 28 to obtain the baseline information. The system may comprise a contact detection capability using a proximity signal such as an optical measurement using emitter/receiver architecture. Contact may be defined as the point where the signal detected by the receiver exceeds a pre-determined value, for example. This may help the system decipher between tissue and teeth when used in the mouth, for example. Many other methods of tissue detection and proximity detection are possible. In a preferred embodiment, a first step in the proposed invention of detecting that the measurement device is in contact with gingival tissue is performed using the optical sensor 28 as follows:

Contact detection using a proximity signal—optical measurement using emitter/receiver architecture—where contact is detected when the signal observed by the receiver exceeds a pre-determined value.

Tissue characterization using the optical properties of gingival tissue, e.g. by color segmentation using a color ratio either over a specific band of wavelength (e.g. red over green) or a dedicated set of wavelength (e.g. ratio 480 over 660 nm).

At step 530 of the method, a force is applied to the tissue by the force-generation module 52 of the oral care device 10. Force-generation module 52 applies a burst of compressed air or a burst of liquid to the tissue. Using liquid to apply force may result in specular reflections which could reduce the signal to noise ratio of the measurement, and thus compressed air might be preferred in some embodiments.

Oral care device 10 may comprise a plurality of sensors 28 and a plurality of force-generation modules 52. The sensors and force-generation modules may all work together in tandem, or they may operate individual or in small clusters depending on one or more parameters such as the location within the mouth, the proximity of tissue, and others.

At step 540 of the method, the sensor 28 of the oral care device obtains an optical signal from the tissue to which pressure has been applied. Once the force has been applied, the sensor collects one or more optical measurements—such as average color values or reflectivity values obtained at one or more wavelengths—to characterize the response of the tissue over time. The sensor may stop obtaining measurements when the collected time series reaches a stable level, such as below a predetermined threshold. Alternatively, the sensor may stop obtaining measurements after a predetermined period of time, such as milliseconds or seconds.

Figure 6:
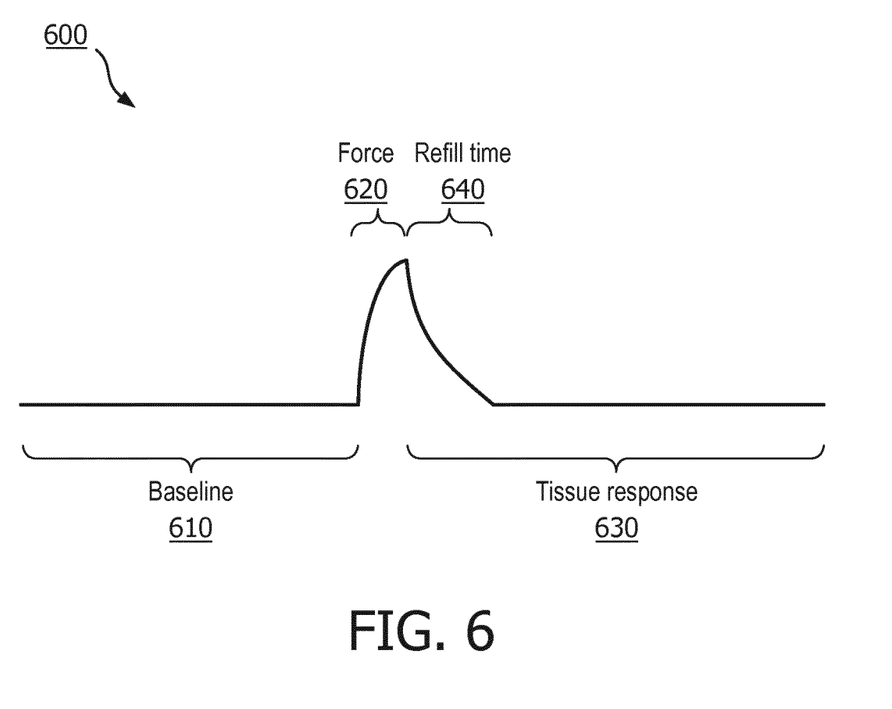
FIG. 6 is a graph of tissue recovery time following the application of force, in accordance with an embodiment.

Referring to FIG. 6 is a graph 600 of a signal collected from a tissue over time. At time 610, the system obtains baseline information about the tissue, which is one or more optical signals obtained from the tissue. At time 620, force is applied to the tissue. At time 630, the sensor of the device obtains a series of optical signals from the tissue as the tissue refills with blood following the application of pressure. The refill time 640 is the period of time during which the tissue recovers from the application of pressure until it reaches a stable or consistent level, or until it reaches the measured baseline level.

At step 550 of the method, the system quantifies, based at least in part on the obtained optical signals from the tissue, one or more health parameters of the user. For example, based on the obtained information and the capillary refill time, the system determines that the tissue is inflamed. Controller 30 of the oral care device 10 may analyze the obtained information to determine whether the analyzed tissue is inflamed. For example, the controller may determine how long it takes for the tissue to reach a stable or consistent level, or how long it takes for the tissue to arrive back at an obtained baseline level.

The metric used to characterize the inflammation level may be obtained by quantifying the time between the maximum signal value—induced by the external force—and the moment the tissue response reaches a stable level, or the moment the tissue reaches the baseline level. The measurement principle used is based on the vasodilation response of the tissue. The vasodilation response can be detected by applying pressure to the tissue, which causes expulsion of blood from the tissue, and then observing the refill. This is termed the capillary refill time. This time is directly correlated to the blood perfusion level of the observed tissue, and a rapid refill time indicates high blood perfusion, which in turn is indicative of a higher inflammation level. Indeed, when tissues are inflamed the vessels tend to dilate which increases blood perfusion and lowers capillary refill time. However, the system can utilize any predefined or programmed correlation or correlation factor.

For example, the system or device calculates the capillary refill time (CRT) using Equation 1:

$$CRT = T_0 - T_1 \quad \text{(Eq. 1)}$$

where $T_0$ correspond to the time where the maximum is observed, and $T_1$ correspond to the moment the absolute value of the signal is below a pre-determined threshold, is stable, or is substantially equivalent to the baseline level.

The system or device may compare the CRT to a database of CRT times correlated to an inflammation level. The database may comprise, for example, a table of CRT/inflammation level correlations, or the system may comprise an algorithm that analyzes one or more CRT values and determines a likely inflammation level.

In addition to an inflammation level, the system or device can quantify a wide variety of other health parameters. The system or device can utilize the method described or otherwise envisioned herein to quantify health parameters such as hydration of the tissue and/or a variety of other local or systemic health parameters.

At step 560 of the method, the system or device provides feedback to the user regarding the quantified health parameter. The user interface/feedback module 46 of the oral care device 10, for example, can provide direct and/or indirect feedback to the user while the oral care device is being used, or after a cleaning session. As an example, the device can provide direct feedback to the user after each measurement using audio, visual, haptic, and/or digital feedback whenever inflammation is detected, or whenever an inflammation level above a predetermined value is detected. As another example, the device can provide direct feedback to the user via audio, visual, haptic, and/or digital feedback only when an inflammation level above a predetermined value is detected by two or more sensors. This may prevent false positive alerts. The predetermined inflammation level may be based on a variety of factors, including but not limited to the baseline information obtained by the device, a set of measurements obtained over time, an external source such as a dental professional, and other factors.

The system or device may provide feedback to the user after a cleaning session is complete. As an example, the system or device may provide feedback once a cleaning session is complete by means of visual representation where the inflammation levels are displayed. The feedback may include, for example, a mouth map—using location sensing technology during measurement—either in their absolute form to show the inflammation levels or in relative forms to highlight one or more specific sites. To that end, the sensors 28 can comprise, for example, a 6-axis or a 9-axis spatial sensor system, and can include one or more of an accelerometer, a gyroscope, and/or a magnetometer to provide readings relative to axes of motion of the oral care device, and to characterize the orientation and displacement of the device. For example, the sensor 28 can be configured to provide readings of six axes of relative motion (three axes translation and three axes rotation), using for example a 3-axis gyroscope and a 3-axis accelerometer. According to an embodiment, sensor 28 is configured to generation information indicative of the acceleration and angular orientation of the oral care device 10. For example, the sensor system may comprise two or more sensors 28 that function together as a 6-axis or a 9-axis spatial sensor system. According to another embodiment, an integrated 9-axis spatial sensor can provide space savings in an oral care device 10.

At optional step 570 of the method, the quantified health parameter is stored and/or communicated with a third party, either locally or remotely. For example, a patient may be instructed to use the oral care device during an appointment with a dental care professional, to assess inflammation. The inflammation information will then be communicated to the dental care professional, using a report or other mechanism. As another example, a user may collect health parameter information that is automatically or periodically transmitted to a remote healthcare professional or other intended or authorized entity where it can be analyzed continuously or during an appointment with the user.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited. In the claims, as well as in the specification above, all transitional phrases such as "comprising," "including," "carrying," "having," "containing," "involving," "holding," "composed of," and the like are to be understood to be open-ended, i.e., to mean including but not limited to.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The invention claimed is:

1. An oral care device configured to assess a health parameter of gingival tissue of a user, the oral care device comprising:
   a force-generating module configured to apply a momentary force to the gingival tissue by applying a burst of compressed air or a burst of liquid to the gingival tissue;
   a sensor configured to obtain a plurality of optical signals from the gingival tissue over time after the momentary force has been applied;
   a controller configured to quantify, based at least in part on an analysis of the plurality of optical signals, a health parameter of the gingival tissue, wherein the health parameter is based at least in part on an amount of time the gingival tissue takes to recover to the application of force; and
   a feedback module configured to provide information to the user indicative of a health condition of the gingival tissue detected by the quantified health parameter based at least in part on an amount of time the gingival tissue takes to recover to the application of force.

2. The oral care device of claim 1, wherein the sensor is further configured to a baseline optical signal from the tissue prior to the application of force.

3. The oral care device of claim 2, wherein the controller is configured to determine an amount of time the gingival tissue takes to substantially match the obtained baseline optical signal.

4. The oral care device of claim 1, wherein the sensor comprises a light source and an optical sensor.

5. The oral care device of claim 1, wherein the force-generating module is configured to apply force via the expulsion of air.

6. The oral care device of claim 1, wherein the controller is configured to determine an amount of time the tissue takes to reach a predetermined perfusion threshold following the application of force, or an amount of time the tissue takes to reach a stable perfusion level following the application of force.

7. The oral care device of claim 1, wherein the health parameter is inflammation of the gingival tissue.

8. An oral care method for assessing a health parameter of gingival tissue of a user by means of an oral care device, the oral care method comprising the steps of:
   applying a momentary force to the gingival tissue by applying a burst of compressed air or a burst of liquid to the gingival tissue;
   obtaining after the momentary force has been removed, a plurality of optical signals from the gingival tissue over time;
   quantifying, based at least in part on the plurality of optical signals, a health parameter of the gingival tissue, wherein the health parameter is based at least in part on an amount of time the gingival tissue takes to recover to the application of force; and
   providing information to the user indicative of a health condition of the gingival tissue detected by the quantified health parameter based at least in part on an amount of time the gingival tissue takes to recover to the application of force.

9. The oral care method of claim 8, further comprising the step of obtaining a baseline optical signal from the tissue prior to the application of force.

10. The oral care method of claim 8, further comprising the step of detecting a proximity to the gingival tissue.

11. The oral care method of claim 8, further comprising the step of communicating the quantified health parameter to a remote third party.

12. The oral care method of claim 8, wherein the applying step includes applying force via the expulsion of air.

13. The oral care method of claim 8, wherein the step of quantifying a health parameter of the user comprises a determination of an amount of time the tissue takes to reach a predetermined perfusion threshold following the application of force, or an amount of time the tissue takes to reach a stable perfusion level following the application of force.

14. The oral care method of claim 9, wherein the step of quantifying a health parameter of the user comprises a determination of an amount of time the gingival tissue takes to substantially match the obtained baseline optical signal.

15. The oral care method of claim 8, wherein the health parameter is inflammation of the gingival tissue.

* * * * *